United States Patent
Kulkarni et al.

(10) Patent No.: US 10,054,597 B2
(45) Date of Patent: Aug. 21, 2018

(54) METHOD FOR IDENTIFYING AND QUANTIFYING CARBOXYETHYL VALINE MODIFIED HAEMOGLOBIN

(71) Applicant: Council of Scientific & Industrial Research, New Delhi (IN)

(72) Inventors: Mahesh Jagdishrao Kulkarni, Pune (IN); Jagadeeshaprasad Guddadarangaiah Mashanipalya, Pune (IN); Kedar Balaji Batkulwar, Pune (IN); Moneesha Fernandes, Pune (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 15/254,539

(22) Filed: Sep. 1, 2016

(65) Prior Publication Data
US 2017/0074888 A1    Mar. 16, 2017

(30) Foreign Application Priority Data
Sep. 1, 2015   (IN) ............... 2730/DEL/2015

(51) Int. Cl.
*G01N 33/68*   (2006.01)
*G01N 33/72*   (2006.01)

(52) U.S. Cl.
CPC ....... *G01N 33/6848* (2013.01); *G01N 33/721* (2013.01); *G01N 2800/042* (2013.01)

(58) Field of Classification Search
CPC ......... G01N 2800/042; G01N 33/6848; G01N 33/721
See application file for complete search history.

(56) References Cited

PUBLICATIONS

Badoud et al. Mass spectrometric analysis of N-carboxymethylamino acids as periodate oxidation derivatives of Amadori compounds—Application to glycosylated haemoglobin. Amino Acids, 1993. vol. 5, pp. 367-375. (Year: 1993).*

Jagadeeshaprasad et al. Targeted quantification of N-1-(carboxymethyl) valine and N-1-(carboxyethyl) valine peptides of β-hemoglobin for better diagnostics. Clinical Proteomics, 2016. vol. 13, No. 7, pp. 1-11. (Year: 2016).*

Uchimura et al. Elevation of N-(Carboxymethyl)valine Residue in Hemoglobin of Diabetic Patients. Diabetes Care, May 2001. vol. 24, No. 5, pp. 891-896. (Year: 2001).*

Cai et al. Identification and Quantitation of N-(Carboxymethyl)valine Adduct in Hemoglobin by Gass Chromatography/Mass Spectrometry. J Mass Spectrom, 1999. vol. 34, Issue 5, pp. 537-543. (Year: 1999).*

Jagadeeshaprasad et al., "Targeted quantification of N-1-(carboxymethyl) valine and N-1-(carboxyethyl) valine peptides of β-hemoglobin for better diagnostics in diabetes", Clin. Proteomics, 13:7, Mar. 29, 2016.

Peppa et al., "Glucose, Advanced Glycation End Products, and Diabetes Complications: What Is New and What Works." Clinical Diabetes, vol. 21, No. 4, pp. 186-187, Oct. 2003.

* cited by examiner

*Primary Examiner* — Marcela M Cordero Garcia
(74) *Attorney, Agent, or Firm* — Lerner, David, Littenberg, Krumholz & Mentlik, LLP

(57) ABSTRACT

The present invention relates to a method for identification and quantification of carboxyethylated valine modified haemoglobin to assess the extent of diabetic complications.

4 Claims, 4 Drawing Sheets

METHOD FOR IDENTIFYING AND QUANTIFYING CARBOXYETHYL VALINE MODIFIED HAEMOGLOBIN

TECHNICAL FIELD OF THE INVENTION

The present invention relates to a method for identification and quantification of carboxyethylated valine modified haemoglobin to assess the glycemic status in diabetic individuals.

Further, the present invention relates to development of a diagnostic kit for detecting the glycemic status and extent of glycation in diabetes in a diseased individual by estimating the carboxyethylated valine modified haemoglobin.

BACKGROUND AND PRIOR ART OF THE INVENTION

Diabetes mellitus is a major and growing health problem in most of the countries. Globally, over the past three decades, the number of individuals with diabetes mellitus has more than doubled, making it one of the foremost public health challenges to all nations. According to estimation by the International Diabetes Foundation, around 592 million people will be affected with diabetes by the year 2040. In India the number of adults suffering from diabetes is expected to increase three-fold, from 19.4 million in 1995 to 57.2 million in 2025. In recent times Type 2 diabetes mellitus (T2DM) and prediabetes are observed to have an increasing incidence among children, adolescents and younger adults. The causes of such epidemic like situation of T2DM are embedded in a very complex group of genetic and epigenetic systems interacting within an equally complex societal framework and intrauterine system which determines environmental influences.

Patients diagnosed with diabetes are susceptible to a range of complications during their life time. Diabetes is addressed to be the leading cause of complications including blindness or retinopathy, amputations, renal dysfunction and neurodegenerative disorders such as diabetic neuropathy. A distinct example of diabetic complications is mirrored in diabetic vascular complications which is the leading cause of end stage renal failure, retinopathy, neuropathies and accelerated atherosclerosis, which accounts for disabilities and high mortality rates in diabetic patients. The etiology of these diabetic complications is poorly understood.

A large body of evidence relating to research investigations have suggested the formation of Advanced Glycation End products (AGE's) to be the leading cause in the development of diabetic complications. For instance AGEs are found in retinal vessels of diabetic patients, and their levels correlate with that in serum as well as with severity of retinopathy. AGE's are a heterogenous group of molecules formed by a series of non-enzymatic reactions between reducing sugars and proteins, especially glucose and glucose derived products which are major glycating agents in hyperglycemic conditions with free amino groups of proteins, lipids, and nucleic acids. The initial product of this reaction is called a Schiff base, which spontaneously rearranges itself into an Amadori, i.e. a deoxufructosylated product, as is the case of the well-known haemoglobin A1c (A1C). A series of subsequent reactions, including successions of dehydrations, oxidation-reduction reactions, and other arrangements lead to the formation of AGEs. Several compounds, e.g., N-carboxymethyl-lysine, N-carboxyethyl-lysine, pentosidine, or methylglyoxal derivatives, serve as examples of well-characterized and widely studied AGEs. (Melpomeni Peppa et al, *Clinical diabetes*, Vol 21, 4, 2003)

A crucial characteristic of AGE's is their ability for covalent crosslink formation between proteins, resulting in alteration of protein structure and function, as in cellular matrix, basement membranes, and vessel-wall components. Other major features of AGE's relate to their interaction with variety of cell-surface AGE-binding receptors, leading either to endocytosis and degradation or to cellular activation and pro-oxidant, pro-inflammatory events.

Prevention of T2DM is a 'whole-of-life' task and requires an integrated approach operating from the origin of the disease. Future research is necessary to better understand the potential role of remaining factors, such as genetic predisposition and maternal environment, to help shape prevention programs. The potential effect on global diabetes surveillance of using glycated haemoglobin (Hb) $HbA_{1c}$ rather than glucose values in the diagnosis of T2DM is well known.

HbA1c/deoxyfructosylated-N1-Val-β-Hb is believed to reflect the glycemic status over the preceding eight to ten weeks. Depending on the estimation method used, HbA1c concentration ranges from 3 to 6.5% of total haemoglobin in normal individuals to as high as 15% in individuals with diabetes. The previous studies have suggested that HbA1c is slowly reversible, and for a given glucose concentration the HbA1c content of red blood cells ultimately reaches an equilibrium value. This suggests that HbA1c does not exactly correlate with the glucose levels in diabetes. HbA1c/deoxyfructosylated-N1-Val-β-Hb, an early product during glycation reaction can undergo carboxymethylation and carboxyethylation Additionally, glycation is a dynamic reaction; the deoxyfructosylation which is the first and reversible modification of glycation, undergoes various structural rearrangements oxidation, dehydration, condensation, fragmentation, or cyclization leading to the formation of AGEs like carboxymethylation and carboxyethylation. Further, highly reactive dicarbonyls such as glyoxal, methylglyoxal, and 3-deoxyglucose are formed during glycation reaction, which in turn react with proteins and form cross-linked AGE's. Therefore, it is possible that haemoglobin can undergo various AGE modifications referred to as AGE-HbA, as it is one of the long lived blood proteins. The extent of AGE-HbA formation may increase with severity of hyperglycemic condition in diabetes. However, the current diagnostic approaches measure only deoxyfructosylated-N1-Val-β-Hb (HbA1C) and do not measure other AGE-HbA.

The current approaches employed to measure HbA1c levels in human blood include boronate affinity chromatography, HbA1c-specific immunoassays and Ion-exchange based separation. Boronate affinity chromatography detects the presence of cis-diol groups of glycated haemoglobin, therefore levels of Deoxyfructosylation modified haemoglobin which contain the cis-diol group, can be detected, while different other forms of AGEs such as carboxymethylation and carboxyethylation, etc. that are formed during advanced glycation, do not contain the cis-diol group and therefore their levels are unaccounted for in the analysis of glycated haemoglobin. Immunoassays involve the detection of glycation of N-terminus valine residue of the β-chain of the haemoglobin using specific antibodies. By and large the antibodies are raised against only Deoxyfructosylation modification, and therefore the other modifications are not detected. In case of ion-exchange based separation of HbA1C, the amino acid modifications in haemoglobin variants such as Sickle cell haemoglobin, haemoglobin variants D and E also cause a similar change in the net charge as that of the glycated haemoglobin (AGE-HbA) molecule. Thus they can interfere in separation of HbA1c and may lead to over estimation. Additionally, the AGE-HbA may also interfere in analysis as these are quite heterogeneous.

Keeping in mind the crucial role AGE modified haemoglobin serves in diabetic complications and the need to estimate its concentration at regular intervals in diabetics, the present inventors have by employing mass spectrometry characterized the AGE modification of N-terminus valine and other lysine residues of haemoglobin, thus indicating the quantification of AGE-HBA to be a better strategy to assess the glycemic status in diabetic patients.

OBJECT OF THE INVENTION

The main objective of the present invention is to provide a process for the identification and quantification of carboxyethyl valine modified haemoglobin to assess the severity of diabetes.

Another object of the present invention is to provide a process for the quantification of carboxyethyled valine modified peptides of haemoglobin in human blood to indicate the state of diabetes i.e. microalbuminuria, pre-diabetic, diabetic, and in poorly controlled diabetes.

SUMMARY OF THE INVENTION

The present invention provides a process for the identification and quantification of Advanced Glycation end products i.e. carboxyethyled valine modified haemoglobin to assess the extent of diabetic complications in a disease individual.

In this aspect, the present invention provides a process for identifying and quantifying carboxyethylated level of haemoglobin in biological fluids comprising; (a) subjecting the biological fluid to mass spectrometry to generate fragment ions; (b) identifying the specificity of fragment ions obtained in step (a), to quantify carboxyethyled modified valine residues in alpha and beta chains of haemoglobin by comparing the said fragment ions with signature ions in the diagnostic fragment ion library In another aspect, the present invention provides a process for identifying and quantifying carboxyethyled valine modified haemoglobin level in blood.

In an embodiment, the present invention provides a process for identifying and quantifying carboxyethyl valine peptides of haemoglobin in biological fluids comprising;
    (a) creating a reference signature fragment ion library for carboxyethyl valine modified haemoglobin such that carboxyethyl modified valine site of Seq Id No. 1, is the N-terminal valine at the first amino acid position; and carboxyethyl modified valine site of Seq Id No. 2, is the N-terminal valine at the first amino acid position;
    (b) subjecting fragment ions of the biological fluid generated by mass spectrometry;
    (c) identify carboxyethyl valine modified haemoglobin in Seq Id No. 1 and Seq Id No. 2 by comparing the said fragment ions with signature ions in the fragment ion library;
    (d) further quantifying the carboxyethyl valine modified haemoglobin content by tandem mass spectrometric approaches such as MRM, PRM, SWATH.

In another embodiment, the reference ion library is constructed by subjecting in-vitro carboxyethyl valine modified haemoglobin to mass spectrometry to obtain signature fragment ions.

In still another embodiment, the present invention provides a reference fragment ion library comprising fragment ions specific to carboxyethyl modified valine sites of haemoglobin.

In another embodiment, the present invention provides a diagnostic kit to identify the severity of diabetes in an individual by estimating the carboxyethyl valine modified haemoglobin content in a biological fluid; comprising;
    a) hemoglobin peptides subjected to mass spectrometry obtained from individuals;
    b) a chart of the signature fragment ion library specific to the said glycated peptides or loaded into device connected to mass analyzer, comprising (ii) carboxyethylated valine sites of $\alpha$ and $\beta$ chains of haemoglobin selected from the group consisting of amino acid positions of V1, wherein variation in the levels of glycation at the said sites indicate the extent of diabetes;
    c) comparing the fragment ions obtained from step (a) with the reference ion library chart in (b) by tandem mass spectrometry for identifying and quantifying carboxyethylated valine;
    d) peptides to predict severity of diabetes; and
    e) a catalogue containing instructions to use the kit contained in a Product Information Sheet.

In still another embodiment, the biological sample is blood.

In yet another aspect, the present invention provides a diagnostic kit to identify the extent of diabetes in a an individual and thereby estimating the carboxyethylated valine haemoglobin content in blood; comprising;
    (a) a minimally invasive sterilized device to draw out blood from individual which is subjected to fragmentation by mass spectrometry;
    (b) a chart of the signature fragment ion library specific to the said glycated peptides loaded onto a hardware connected to analytical devices e.g. mass analyzer, comprising carboxyethylated/N-terminal valine sites of alpha and beta chains of haemoglobin, wherein variation in the levels of glycation at the said sites indicate the extent of diabetes;
    (c) tandem mass spectrometry such as parallel reaction monitoring (PRM) data acquisition based targeted mass spectrometry software for identifying carboxyethylated valine modified peptides of haemoglobinpeptides; and
    (d) a catalogue containing instructions to use the kit contained in a Product Information Sheet.

The present method can be employed to evaluate the etiology of diabetic complications and classify the diseased individual as pre-diabetic, diabetic or poorly controlled diabetic.

DETAILED DESCRIPTION OF THE INVENTION

Figure 1:
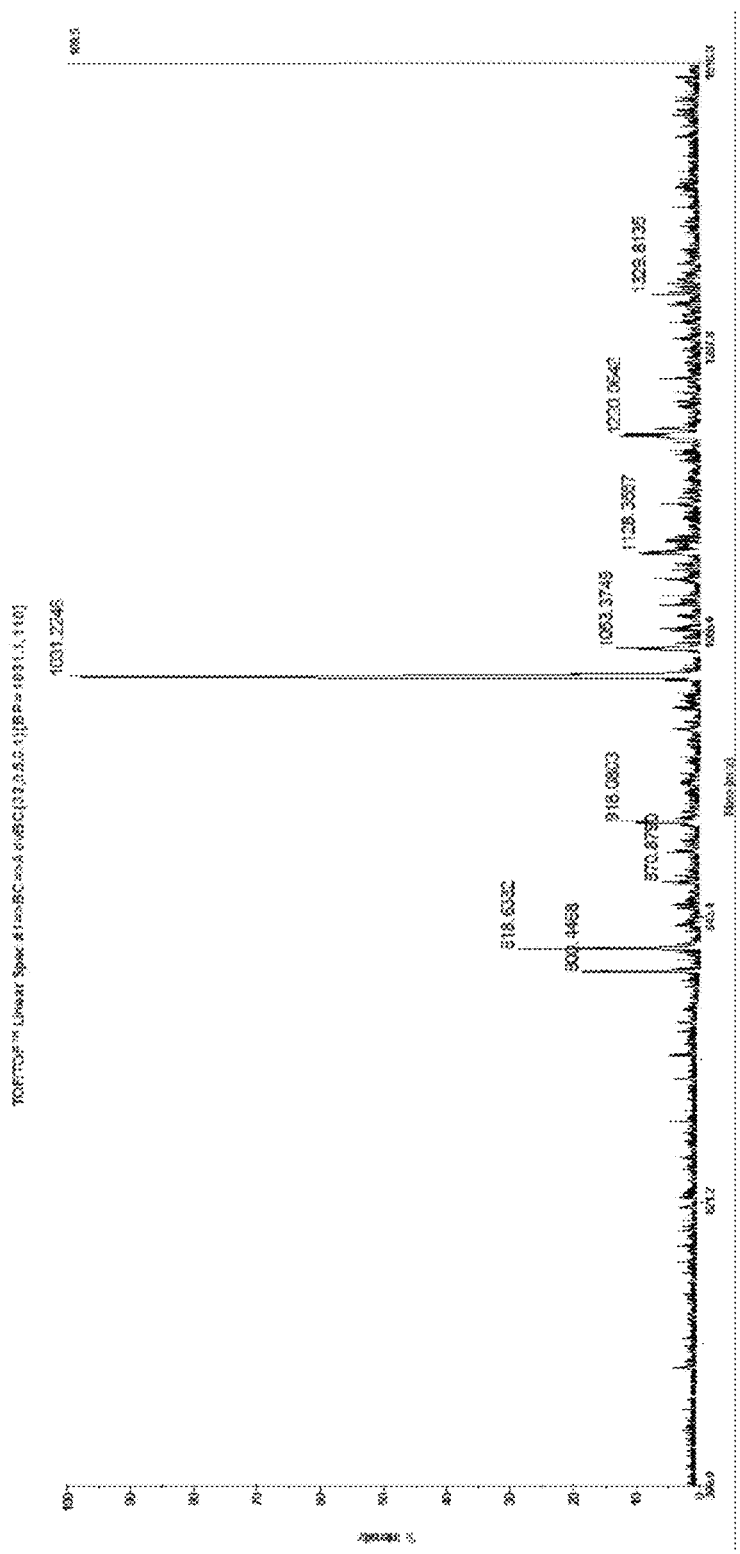
FIG. 1 depicts the MALDI-ToF spectrum of the synthesized peptide (COOH—$CH_2$-VHLTPEEK-OH). Calculated mass (M+)=1009, Observed Mass (M+Na)=1032.

The invention will now be described in detail in connection with certain preferred and optional embodiments, so that various aspects thereof may be more fully understood and appreciated.

In the present specification Amadori modified lysine i.e. AML or deoxyfructosyl modified lysine refer to the same modification and may be used interchangeably.

Further, in the present application, in accordance with the standard alphabetic letters used to represent amino acids, the alphabet K and V referred to in following embodiments represents the amino acid lysine and valine.

In the most preferred embodiment, the present invention provides a process for identifying and quantifying carboxyethylated valine modified haemoglobin in biological fluids comprising; (a) subjecting the biological fluid to mass spectrometry to generate fragment ions; (b) identifying the specificity of fragment ions obtained in step (a) to quantify carboxyethyl valine residues in alpha and beta chains of haemoglobin by comparing the said fragment ions with signature ions in the diagnostic fragment ion library;

Accordingly, the present invention involves subjecting the biological fluid, most preferably human blood to mass spectrometry analysis. This human blood sample can be that of a diabetic individual or that of a person who exhibit symptoms of hyperglycemia or hypoglycemia. The haemoglobin peptides are broken into charged fragments, which are then separated according to their mass-to-charge ratio. Ions of the same mass-to-charge ratio will undergo the same amount of deflection. The mass to charge ratios of the ions generated are observed and compared with that of the fragment ions in a diagnostic fragment ion library which are specific to the glycated sites in haemoglobin. The glycation sites on the hemoglobin are determined. The concentration of the glycated peptide level is determined by Parallel reaction monitoring or multiple reaction monitoring or by tandem mass spectrometric analysis.

The alpha (u) sub-unit chain of haemoglobin is represented by Seq Id No. 1 or has at least 80% sequence identity with Seq Id No. 1 and the beta (β) sub-unit of haemoglobin is represented by Seq Id No. 2 and has at least 80% sequence identity with Seq Id No. 2.

In accordance with this preferred embodiment, the diagnostic ion library is constructed by subjecting in-vitro carboxyethyl valine modified haemoglobin to mass spectrometry to obtain signature fragment ions specific to each glycated site.

The diagnostic ion library containing ions specific to diagnostic glycation sites of Seq Id No. 1 is previously prepared by determining the signature fragment ions according to the mass to charge ratio generated by subjecting the in-vitro carboxyethyl valine modified haemoglobin to mass spectrometry.

Accordingly, blood is withdrawn from a subject or otherwise used from blood banks, followed by haemoglobin separation by methods known in the art. These methods include solid phase extraction, affinity chromatography and traditional methods such as centrifugation and filtration. Also, in vitro Haemoglobin is allowed to react with glucose and other glycating agents such as glyoxylic acid and methylglyoxal at body temperature of 37° C. to obtain AGE modification. Concentrations in the range of 5 to 500 mmol/l of glycating agents selected from the group consisting of glucose, and glyoxylic acid were incubated with haemoglobin to obtain AGE modification in the haemoglobin. The resulting in-vitro AGE-modified hemoglobin's (CML, CEL and AGE-hemoglobin's) and extracted haemoglobin were diluted a cleavable reagent i.e. a reagent used to enhance enzymatic digestion of protein containing a buffer (pH—8.3) followed by dry heat treatment to denature. Denatured proteins were reduced and alkylated in the dark condition at room temperature for 30-35 min, respectively. LC-HR/AM Q-Exactive Orbitrap mass spectrometry instrument was used to create of fragment ion library from in-vitro modified hemoglobin.

In a preferred embodiment, the present invention provides a process for identifying the glycated sites and quantifying the glycated haemoglobin level in biological fluids, wherein the AGE modified glycation sites are selected from the group consisting of carboxy ethylated valine residues.

In an optional embodiment, the level of carboxyethylated modified N-terminal valine of Seq Id No. 1 and Seq Id No. 2 is measured employing the present method.

Accordingly, the sites glycated in the amino acid sequence of haemoglobin having Seq. Id No. 1 and Seq Id No. 2 are preferably, valine sites. These glycated sites are characteristic diagnostic sites which determine the extent of glycation in diabetic complications in a diabetic, or a potential diabetic patient.

The carboxyethylated valine site of the alpha and beta chain of haemoglobin is the N-terminal valine at the first amino acid position of the chain.

Figure 2A:
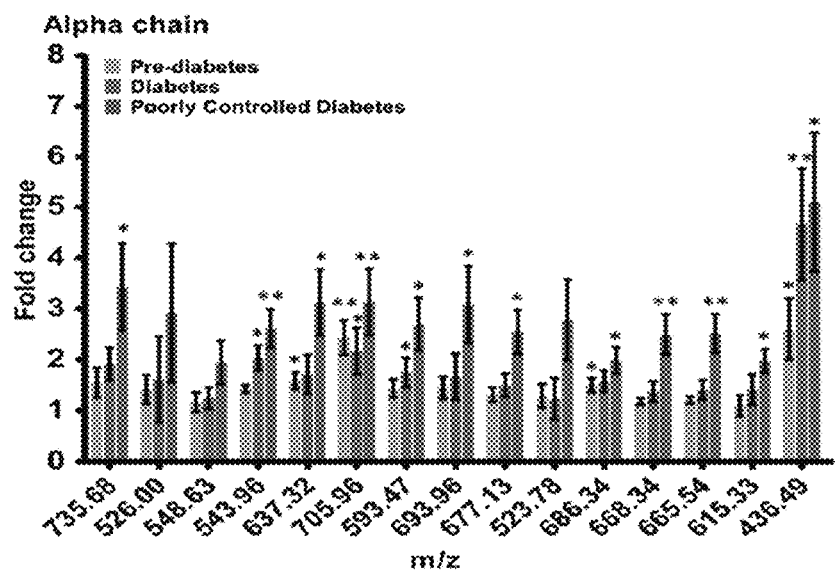
FIG. 2(a) depicts Relative fold change in AUC for glycated peptides of $\alpha$-Hb and FIG. 2(b) depicts Relative fold change in AUC for glycated peptides of $\beta$-Hb with respect to healthy control. Statistical analysis was performed by two-way ANOVA followed by Tukey's test. PD-prediabetes, D-diabetes and PCD-poorly controlled diabetes (*$p<0.05$, $p<0.005$, *$p<0.0005$)
Figure 2B:
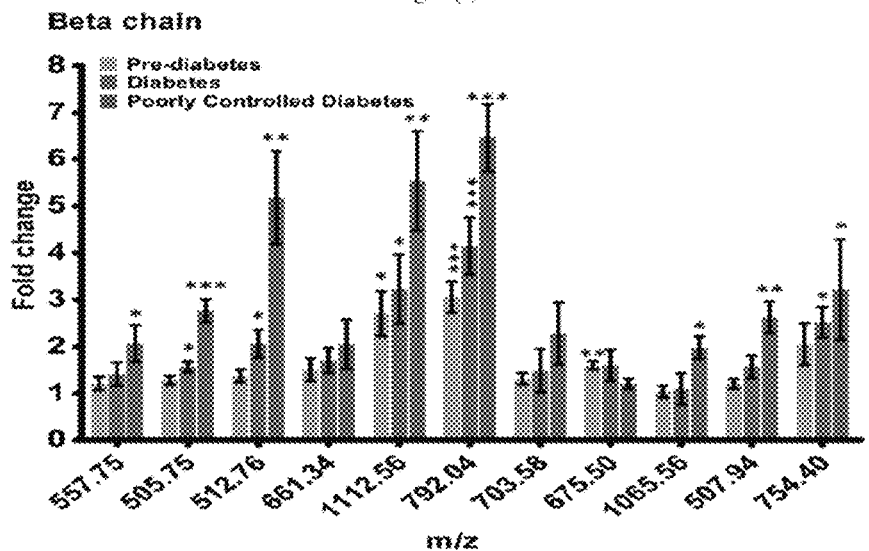
Figure 3A:
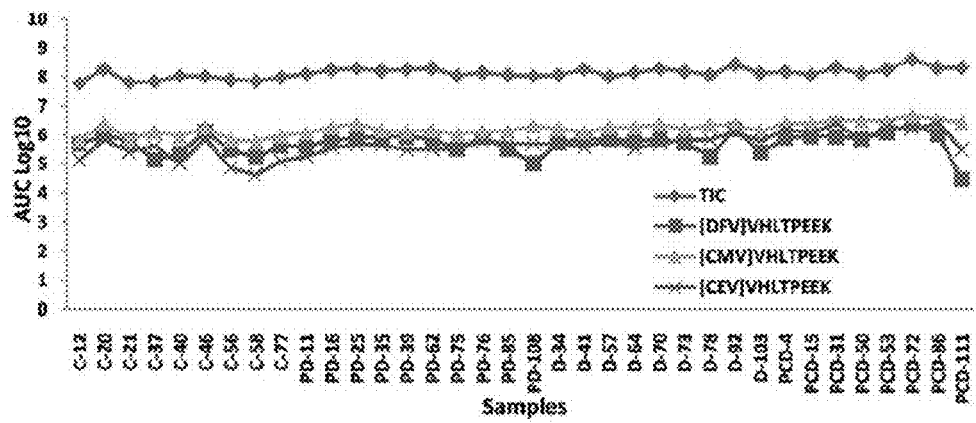
FIG. 3(a) depicts the Log(10) values of average of TIC and average of AUC of CMV, CEV and DFV peptides, indicating that there was no major variation in TIC across different samples, although the AUC of CMV, CEV and DFV increased with severity of diabetes.
Figure 3B:
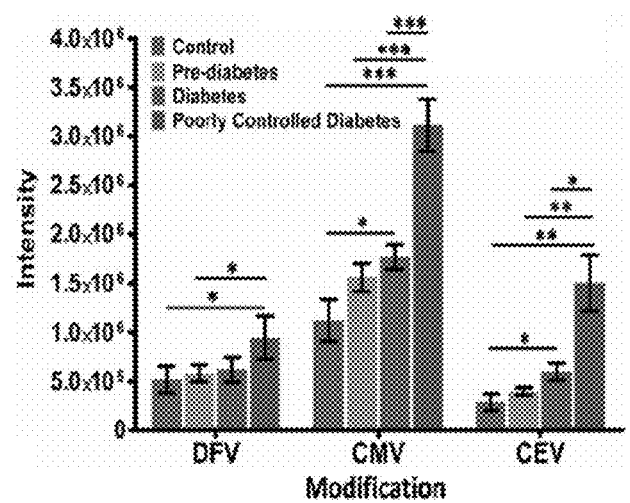
FIG. 3(b) depicts the AUC of DFV, CMV and CEV peptides of β-hemoglobin depicting relative abundance.
Figure 3C:
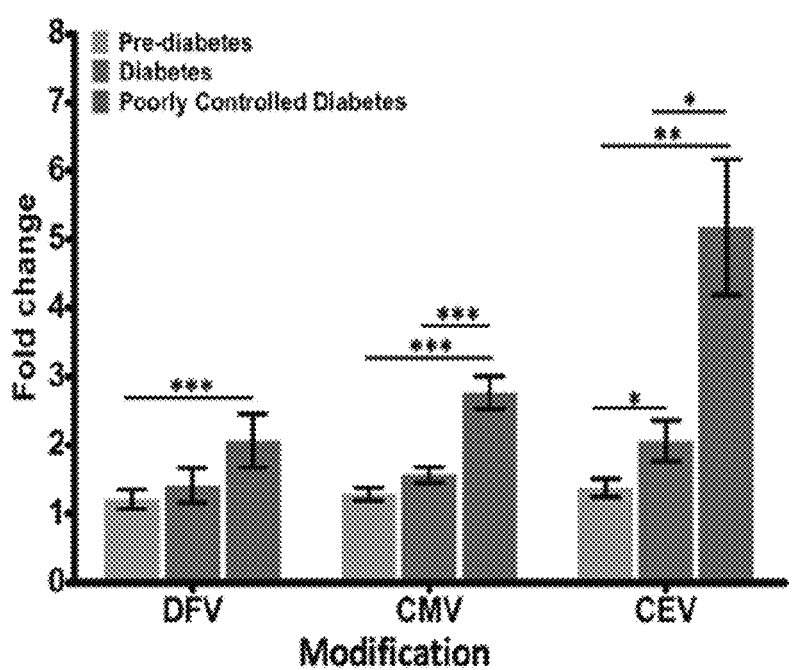
FIG. 3(c) depicts the Relative fold change in AUC for DFV, CMV and CEV peptides of β-hemoglobin by PRM. Statistical analysis was performed by two-way ANOVA followed by Tukey's test and Bonferonnis posttests. Clinical groups are represented as C control, PD prediabetes, D diabetes, PCD poorly controlled diabetes (*p<0.05, p<0.005, *p<0.0005).

The list of modified peptides and their corresponding fragment ions used for quantification is mentioned in Table 1 and Table 2. A total of 26 glycated peptides, i.e. 15 from α-Hb and 11 from β-Hb were identified and quantified in clinical samples (FIGS. 2(a) and (b)). Fold change in AUCs was calculated for all the modified peptides across different clinical conditions and is represented in FIGS. 2(a) and (b). A total of 13 peptides of α-Hb and 9 peptides of β-Hb were significantly elevated in poorly controlled diabetes as depicted in FIG. 2a, b respectively.

Glycated peptides of α-Hb (1) sequence: K*(CM)VADALTNAVAHVDDM(Seq Id No.4)*(Oxd) PNALSALSDLHAHK(Seq Id No.5)*(CM)LR, m/z-705.96, site-K61 and K90;

(2) sequence: K*(CM)VADALTNAVAHVDDMPNALSALSDLHAHK(Seq Id No.6), m/z-640.12, site-K61; and β-Hb (3) sequence: V*(CM)HLTPEEK(Seq Id No.7)*(CM) SAVTALWGK(Seq Id No.8)*(CM)VNVDEVGGEALGR (Seq Id No.9), m/z: 1112.56, site-V1, K8 and K17 and (4) FFESFGDLSTPDAVM(Seq Id No.10)*(Oxd) GNPK (Seq Id No.11)*(CEL)VK, /z: 792.04, site-K61 showed significant increase in all the diabetic conditions.

In another preferred embodiment, the present invention provides a process for identifying carboxyethylated valine (CEV) residues in hemoglobin.

On identifying the carboxyethylated peptide level in a diseased individual, the extent of diabetes in an individual is estimated. The pre-diabetic stage, diabetes and poorly controlled diabetes are indicated.

In an embodiment the present invention provides a diagnostic ion library comprising fragment ions specific to glycation sites of haemoglobin.

The signature fragment ion library specific to the glycated site of haemoglobin sub-unit is indicated in Tables 1, 2 and 3 below.

In one more preferred embodiment, the present invention provides a diagnostic kit to identify the extent of diabetes in a diseased individual and thereby estimating the carboxyethyl glycated haemoglobin content in a biological fluid; comprising;
(a) a minimally invasive sterilized device to draw out serum from the diseased individual which is to be subjected to fragmentation by mass spectrometry;
(b) a chart of the signature fragment ion library specific to the said glycated peptides, comprising (i) carboxyethylated N-terminal valine sites of alpha and beta chains of haemoglobin, wherein variation in the levels of glycation at the said sites indicate the extent of diabetes;
(c) parallel reaction monitoring (PRM) data acquisition based targeted mass spectrometry software for identifying carboxyethylated peptides; and
(d) a catalogue containing instructions to use the kit contained in a Product Information Sheet.

The device employed to draw out blood is a heparin/EDTA coated capillary tube.

The present diagnostic kit can be employed by pathologists and physicians to provide the patient with information regarding the gravity of the diabetes. Elevated levels of glycated haemoglobin in both the alpha and beta chain can be used to direct patients in early stages of diabetes or patients having micoralbuminuria to monitor diet.

In another embodiment, the percent carboxyethylated haemoglobin levels may be estimated by MRM (Multiple reaction monitoring)/PRM (Parallel reaction monitoring)/SWATH (Sequential Window Acquisition of all Theoretical Fragment Ion Spectra)/$MS^E$ methods.

In one more embodiment, the present invention provides a method for using the present diagnostic kit comprising either drawing blood from a diseased individual or a person exhibiting symptoms of hyperglycemia or hypoglycemia. Subsequently the blood sample is placed on mass spectrometry target plate, along with dried spots of a positive control containing in-vitro synthesized AGE modified haemoglobin and negative control of haemoglobin in the neighbouring space available in the target plate. The samples are subjected to mass spectrometry and the fragment ions generated are observed and compared with that of the diagnostic ion library.

In yet another embodiment, the present invention provides the use of the diagnostic kit in identifying the extent of diabetic complications in a subject, by classifying the diabetic stage to be pre-diabetic, current diabetic stage and poorly controlled diabetic stage in the said subject.

In one preferred embodiment, the present invention provides a peptide conjugated to the AGE modified i.e. carboxymethyl modified hemoglobin, wherein the said peptides have antibody binding affinity. Accordingly, a peptide is synthesized and is conjugated to), carboxyethylated valine (CEV) residues in hemoglobin. Antibodies and ligands specific to the peptide conjugated are generated by conventional methods known in the art.

The peptides synthesized are selected from synthetically generated peptides using solid phase synthesis method. These peptides are oligopeptides having eight to fifty amino acids in the peptide sequence.

One of the peptides conjugated to the AGE modified amino acid residues of hemoglobin in the present invention is an oligopeptide having Seq Id No. 3 i.e. carboxymethylated-VHLTPEEK was synthesized.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Construction of Diagnostic Ion Library (i) Synthesis of AGE Modified Haemoglobin by In-vitro Methods
(a) Haemoglobin Extraction
By using heparin-coated capillary tube, the blood was collected from retro-orbital vascular plexus of a subject. The blood was dispensed in tubes containing aprotinin and mixed within the same capillary tube and later capped. The blood was further mixed after capping followed by centrifugation at 3000 rpm for 15 min. The erythrocytes in the lower layer were washed three times with saline buffer and then stored at −80° C. until use. A volume of 25 μl of erythrocyte was added to a solution of 20 μl of 0.1% Rapigest (in 50 mM ammonium bicarbonate buffer pH—8.3) and 15 μl of 50 mM ammonium bicarbonate buffer pH—8.3. This mixture was intermittently vortexed for about 30 minutes in freezing conditions, followed by centrifugation at 17000 rpm for 60 minutes. The supernatant was collected and centrifugation was repeated followed by protein estimation by Bradford protein assay method.
(b) Synthesis of Carboxymethylated/Carboxyethylated-Haemoglobin
A solution of 10 mg/ml human haemoglobin and sodium cyanoborohydride (0.05 M) were dissolved in 0.2 M phosphate buffer (pH 7.4), to which glyoxylic acid (carboxymethylated) or methylglyoxal (carboxyethylated) (0.045 M) was added and final volume was made up 1 ml with 0.1M phosphate buffer, the reaction mixture was incubated at 37° C. for 24 hours under sterile and dark conditions.
(c) Synthesis of AGE-Haemoglobin
10 mg/ml human haemoglobin was incubated with varying (5, 20 and 500 mmol/l (normoglycemic and hyperglycemic conditions)), concentrations of glucose in 0.2 M phosphate buffer (pH 7.4). The samples were incubated at 37° C. for 15 days under sterile and dark conditions.
(d) Control Haemoglobin was Prepared
10 mg/ml human haemoglobin was incubated with 0.2 M sodium phosphate buffer (pH 7.4). The samples were incubated at 37° C. for 15 days under sterile and dark conditions.
(ii) In-Solution Tryptic Digestion:
Prior to digestion, modified haemoglobin samples were passed through 3 Kd cut-off filters to remove excess of glucose against 0.2M phosphate buffer. The protein content was estimated by Bradford method using BSA as a standard.

Aliquots measuring 50 µg of control and in-vitro AGE-modified haemoglobin's (CM, CE and AGE-haemoglobin's) and in-vivo extracted haemoglobin were diluted with 0.1% rapigest containing 50 mM ammonium bicarbonate buffer (pH—8.3). The samples were dry heated at 80° C. for 15 minutes to denature proteins. Denatured proteins were reduced and alkylated with 100 mM DTT at 56° C. for 15-20 min and 200 mM iodoacetamide in dark conditions at room temperature for 30-35 min, respectively. The proteins were digested overnight (~16-18 hrs) with proteolytic enzyme Trypsin (Sigma) at 50:1 ratio at 37° C. The digestion of protein was terminated by addition of concentrated HCL, incubated at 37° C. for 15 minutes, Peptide collection was done by centrifuging at 12000 rpm for 20 minutes and collected the supernatant. The supernatant containing peptides were by using C18 zip tip (Millipore, Mass., USA) and enriched peptides were concentrated by speed vac and used for LC-MS.

(iii) LC-MS/MS Analysis

LC-HR/AM Q-Exactive Orbitrap mass spectrometry instrument was used to create of fragment ion library from in-vitro modified haemoglobin.

The speed vac digested peptides were reconstituted in 3% ACN contained 0.1% formic acid, from the reconstitute 1.5 µg of digested peptides were injected into online Accel 1250 UHPLC (Thermo Fisher Scientific) coupled to a Q-Exactive Orbitrap mass spectrometer (Thermo Fisher Scientific). The peptides were separated with Gold C18-reverse phase column (150*2.1 mm, 1.9 µm). The solvent system comprised 100% water and 0.1% formic acid (mobile phase A) and 100% acetonitrile and 0.1% formic acid (mobile phase B). Peptides eluted into mass spectrometry at a flow rate of 350 µl/min with 45 minutes linear gradients of 2 to 40% mobile phase B by maintaining column temperature 40° C.

(iv) Mass Spectrometry Conditions

Hybrid quadruple Q-Exactive Orbitrap MS and MS/MS was performed at a resolution of about 70000 and 17500 full width half maximum (FWHM) using an ESI and the mass error was less than 10 ppm. The eluted peptide spectra were acquired by hybrid quadruple Q-Exactive Orbitrap in a positive mode in data dependent manner a scan mass range of 350-2000 m/z with a scan time of 120 msec. Precursor's ion selectivity was performed at an isolation width of 2 m/z, under fill ratio of 0.3% and dynamic exclusion time of 15 sec. The peptide fragmentation was performed in high energy collision induced dissociation (HCD) cell using normalized HCD at 30 eV.

(v) Development of Ion Library

After LC-HR/AM Q-Exactive Orbitrap mass spectrometric data analysis was performed with Proteome Discover software (PD 1.4.0.288, Thermo Fisher Scientific), A preliminary search of processed samples with sequest-HT as search engine for peptide identification against haemoglobin protein database (UniProt id: P68871 and P69905 respectively), PD identified peptides and fragment mass tolerance with less than 10 ppm and 0.5 Da. Oxidation of methionine and carbamidomethylation of cysteine were searched as variable and fixed modifications, Additionally variable lysine and valine specific glycation modifications AMV/AML (+162.02); CMV/CML (+58.005 Da) and CEV/CEL (+72.021 Da) were considered and enzyme specificity was trypsin and up to two missed cleavages were allowed.

The false positive rate was set to 1% in the PD workflow.

Proteome discover identified glycation modified peptides were manually validated by accurate mass shift in precursor ion due to glycation and presence of three consecutive ions from the condensed modified valine/lysine site considered as true glycation modification. The fragment ions observed are presented in the excel sheet, which could serve as diagnostic ions for quantification of AGE-HbA.

Example 2

Solid phase synthesis of CMV-containing octapeptide COOH—$CH_2$-VHLTPEEK(Seq Id No.3)-OH The protected amino acids (Pentafluorophenyl Pfp esters) were purchased from NovaBiochem. All solvents used during the synthesis of peptides were of peptide synthesis grade and for HPLC, of HPLC grade. The peptide sequence was synthesised following standard Fmoc chemistry on Wang resin. Synthesis was carried out manually. Fmoc group was deprotected by using a solution of 20% piperidine in DMF. Coupling reactions were performed by using 3 equivalents of each amino acid, HOBt and DIPEA (N,N-Diisopropylethylamine) in DMF for 6 h. Successive deprotection and coupling and washing steps were carried out in continuous cycles. Deprotection and coupling reactions were monitored by Kaiser Test. For alkylation of valine on solid support, deprotection of Fmoc followed by coupling reaction with chloroacetic acid in presence of DIPEA was carried out. For this, 3 equivalents each of DIPEA and chloroacetic acid were used.

Example 3

Cleavage and Purification of Peptide

After synthesis of the desired peptide, cleavage from the solid support (Wang resin) was achieved by treating with 50% TFA in DCM for 2 h. After 2 h, the reaction mixture was filtered through a sintered funnel and the resin, washed with TFA. The peptide was precipitated in cold diethyl ether. The peptide was purified by RP-HPLC using an increasing gradient of acetonitrile in water containing 0.1% TFA, and characterized by MALDI-ToF mass spectrometric analysis. The MALDI-ToF spectrum of the purified peptide is shown in FIG. 1.

Advantages of the Invention

The present method provides qualitative and quantitative information for identification of glycation sites including carboxyethylated sites;

The method improves existing glycated level diagnostic strategies;

The present method can be employed to estimate glycated hemoglobin levels in patients with hemodialysis.

On quantifying the peptide content, a long term diabetic can monitor the elevated glycated peptide level and asses the diabetic complication that may be caused.

TABLE 1

| No. | Mod site | Peptide start-end | Peptide sequence | Peptide MH+ Da | Monoisotopic m/z Da (mmu/ppm) | CS | RT | XCorr | MC | Gly Mod | Signature fragment ions | | | | | |
|---|---|---|---|---|---|---|---|---|---|---|---|---|---|---|---|---|
| Glucose induced glycation modifications | | | | | | | | | | | | | | | | |
| Alpha Chain Of Hemoglobin | | | | | | | | | | | | | | | | |
| 1 | V1 | 1-7 | VLSPADK | 891.4652 | 446.23624 Da (-0.9 mmu/-2.02 ppm) | 2 | 9.29 | 1.68 | 0 | AMV | $b^+1$ 262.12852 | $b^{2+}1$ 131.56790 | $b^{2+}2$ 200.09735 | $b^+3$ 408.22416 | $b^+5$ 630.33451 | |
| Beta Chain Of Hemoglobin | | | | | | | | | | | | | | | | |
| 11 | V1 | 1-8 | VHLTPEEK | 1114.56072 | 557.78400 Da (-0.99 mmu/-1.77 ppm) | 2 | 10.74 | 1.66 | 0 | AMV | $b^{2+}1$ 131.56790 | $b^{2+}2$ 200.09735 | $b^+3$ 408.22416 | $b^+3$ 512.27150 | | |
| 12 | V1 | 1-8 | VHLTPEEK | 1010.51164 | 505.75946 Da (-1.85 mmu/-3.66 ppm) | 2 | 11.73 | 2.01 | 0 | CMV | $b^+2$ 295.14009 | | | | $b^+4$ 509.27184 | |

TABLE 2

| Sl.N | Mod site | Peptide start-end | Peptide sequence | Peptide MH+ Da | Monoisotopic m/z Da (mmu/ppm) | CS | RT | XCorr | MC | Gly Mod | Signature fragment ions | | |
|---|---|---|---|---|---|---|---|---|---|---|---|---|---|
| Glyoxylic acid induced glycation modifications (CML) | | | | | | | | | | | | | |
| Alpha Chain Of Hemoglobin | | | | | | | | | | | | | |
| Beta Chain of Hemoglobin | | | | | | | | | | | | | |
| 1 | V-1, K-8 & K-17 | 1-30 | VHLTPEEK SAVTALWG KVNVDEVG GEALGR | 3335.68357 | 1112.56604 Da (+2.67 mmu/+2.4 ppm) | 3 | 28.25 | 6.31 | 2 | CMV + CML + CML | $b^{+2}$ 295.14009 | $b^{2+}8$ 1050.51025 | $b^{+}14$ 1500.76535 |
| Beta Chain Of Hemoglobin | | | | | | | | | | | | | |
| 10 | V-1 | 1-8 | VHLTPEEK | 1010.51720 | 505.76224 Da (+0.93 mmu/+1.84 ppm) | 2 | 11.86 | 1.86 | 0 | CMV | $b^{+2}$ 295.14009 | $b^{+}3$ 408.22416 | |

TABLE 3

| Sl.N | Mod site | Peptide start-end | Peptide sequence | Peptide MH+ Da | Monoisotopic m/z Da (mmu/ppm) | CS | RT | XCorr | MC | Gly Mod | Signature fragment ions | | |
|---|---|---|---|---|---|---|---|---|---|---|---|---|---|
| Methylglyoxal induced glycation modifications (CEL) | | | | | | | | | | | | | |
| Alpha Chain Of Hemoglobin | | | | | | | | | | | | | |
| Beta Chain of Hemoglobin | | | | | | | | | | | | | |
| 5 | V-1, & K-8 | 1-8 | VHLTPEEK | 1096.55088 | 366.18848 Da (-0.42 mmu/-1.13 ppm) | 3 | 11.07 | | 0 | CEV + CEL | $b^{2+}_1$ 86.55205 | $y^{2+}_1$ 110.07061 | $y^{2+}_4$ 287.63959 |
| Beta Chain Of Hemoglobin | | | | | | | | | | | | | |
| 6 | V-1 | 1-8 | VHLTPEEK | 1024.53386 | 512.77057 Da (+1.44 mmu/2.8 ppm) | 2 | 16.98 | | 0 | CEL | $b^{2+}_1$ 86.55205 | | |

```
                            Seq Id No. 1
VLSPADKTNVKAAWGKVGAHAGEYGAEALERMFLSFPTTKTYFPHFDLSH
GSAQVKGHGKKVADALTNAVAHVDDMPNALSALSDLHAHKLRVDPVNFKL
LSHCLLVTLAAHLPAEFTPAVHASLDKFLASVSTVLTSKYR

Seq Id No. 2
VHLTPEEKSAVTALWGKVNVDEVGGEALGRLLVVYPWTQRFFESFGDLST
PDAVMGNPKVKAHGKKVLGAFSDGLAHLDNLKGTFATLSELHCDKLHVDP
ENFRLLGNVLVCVLAHHFGKEFTPPVQAAYQKVVAGVANALAHKYH

Seq Id No.3
VHLTPEEK.

Seq Id No. 4
    VADALTNAVAHVDDM

Seq Id No. 5
    PNALSALSDLHAHK

Seq Id No. 6
    VADALTNAVAHVDDMPNALSALSDLHAHK

Seq Id No. 7
    HLTPEEK

Seq Id No. 8
    SAVTALWGK

Seq Id No. 9
    VNVDEVGGEALGR

Seq Id No. 10
    FFESFGDLSTPDAVM

Seq Id No. 11
    GNPK

Seq Id No. 12
    VLSPADK

Seq Id No. 13
    VHLTPEEKSAVTALWGKVNVDEVGGEALGR
```

---

We claim:

1. A process for identifying and quantifying carboxyethyl valine peptides of haemoglobin in biological fluids comprising;
   (a) creating a reference signature fragment ion library for carboxyethyl valine modified haemoglobin such that carboxyethyl modified valine site of Seq Id No.1, is the N-terminal valine at the first amino acid position; and carboxyethyl modified valine site of Seq Id No.2, is the N-terminal valine at the first amino acid position;
   (b) subjecting the biological fluid to mass spectrometry to generate fragment ions;
   (c) identifying carboxyethyl valine modified haemoglobin in Seq Id No.1 and Seq Id No.2 by comparing the said fragment ions with signature ions in the fragment ion library; and
   (d) quantifying the carboxyethyl valine modified haemoglobin content by tandem mass spectrometric selected from the group consisting of MRM (Multiple Reaction Monitoring), PRM (Parallel Reaction Monitoring), and SWATH (Sequential Window Acquisition of all Theoretical Fragment Ion Spectra).

2. The process according to claim 1, wherein the reference ion library is constructed by subjecting in-vitro carboxyethyl valine modified haemoglobin to mass spectrometry to obtain signature fragment ions.

3. The process according to claim 1 wherein the reference signature fragment ion library comprises fragment ions specific to carboxyethyl modified valine sites of haemoglobin.

4. The process as claimed in claims 1 or 2, wherein the biological sample is blood.

* * * * *

SEQUENCE LISTING

<160> NUMBER OF SEQ ID NOS: 13

<210> SEQ ID NO 1
<211> LENGTH: 141
<212> TYPE: PRT
<213> ORGANISM: Artificial Sequence
<220> FEATURE:
<223> OTHER INFORMATION: carboxyethyl modified valine site

<400> SEQUENCE: 1

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 2
<211> LENGTH: 146
<212> TYPE: PRT
<213> ORGANISM: Artificial Sequence
<220> FEATURE:
<223> OTHER INFORMATION: carboxyethyl modified valine site

<400> SEQUENCE: 2

Val His Leu Thr Pro Glu Glu Lys Ser Ala Val Thr Ala Leu Trp Gly
1               5                   10                  15

```
Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 8
<212> TYPE: PRT
<213> ORGANISM: Artificial Sequence
<220> FEATURE:
<223> OTHER INFORMATION: carboxymethylated-VHLTPEEK

<400> SEQUENCE: 3

Val His Leu Thr Pro Glu Glu Lys
1               5

<210> SEQ ID NO 4
<211> LENGTH: 15
<212> TYPE: PRT
<213> ORGANISM: Artificial Sequence
<220> FEATURE:
<223> OTHER INFORMATION: Peptides

<400> SEQUENCE: 4

Val Ala Asp Ala Leu Thr Asn Ala Val Ala His Val Asp Asp Met
1               5                   10                  15

<210> SEQ ID NO 5
<211> LENGTH: 14
<212> TYPE: PRT
<213> ORGANISM: artificial sequence
<220> FEATURE:
<223> OTHER INFORMATION: Peptides

<400> SEQUENCE: 5

Pro Asn Ala Leu Ser Ala Leu Ser Asp Leu His Ala His Lys
1               5                   10

<210> SEQ ID NO 6
<211> LENGTH: 29
<212> TYPE: PRT
<213> ORGANISM: Artificial Sequence
<220> FEATURE:
<223> OTHER INFORMATION: Peptides

<400> SEQUENCE: 6

Val Ala Asp Ala Leu Thr Asn Ala Val Ala His Val Asp Asp Met Pro
1               5                   10                  15
```

Asn Ala Leu Ser Ala Leu Ser Asp Leu His Ala His Lys
            20                  25

<210> SEQ ID NO 7
<211> LENGTH: 7
<212> TYPE: PRT
<213> ORGANISM: Artificial Sequence
<220> FEATURE:
<223> OTHER INFORMATION: Peptides

<400> SEQUENCE: 7

His Leu Thr Pro Glu Glu Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Peptides

<400> SEQUENCE: 8

Ser Ala Val Thr Ala Leu Trp Gly Lys
1               5

<210> SEQ ID NO 9
<211> LENGTH: 13
<212> TYPE: PRT
<213> ORGANISM: Artificial Sequence
<220> FEATURE:
<223> OTHER INFORMATION: Peptides

<400> SEQUENCE: 9

Val Asn Val Asp Glu Val Gly Gly Glu Ala Leu Gly Arg
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Peptides

<400> SEQUENCE: 10

Phe Phe Glu Ser Phe Gly Asp Leu Ser Thr Pro Asp Ala Val Met
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: Peptides

<400> SEQUENCE: 11

Gly Asn Pro Lys
1

<210> SEQ ID NO 12
<211> LENGTH: 7
<212> TYPE: PRT
<213> ORGANISM: Artificial Sequence
<220> FEATURE:
<223> OTHER INFORMATION: Peptides

<400> SEQUENCE: 12

Val Leu Ser Pro Ala Asp Lys

-continued

```
<210> SEQ ID NO 13
<211> LENGTH: 30
<212> TYPE: PRT
<213> ORGANISM: Artificial Sequence
<220> FEATURE:
<223> OTHER INFORMATION: Peptides

<400> SEQUENCE: 13

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg
            20                  25                  30
```